(12) United States Patent
Koga et al.

(10) Patent No.: US 6,840,899 B2
(45) Date of Patent: Jan. 11, 2005

(54) METHOD AND INSTRUMENT FOR SURGICAL DELIVERY OF BIOCOMPATIBLE MATERIALS

(75) Inventors: Margaret C. Koga, Moorpark, CA (US); Mark Edward Apgar, Oxnard, CA (US); William R. Pratt, Newbury Park, CA (US)

(73) Assignee: Kinamed, Inc., Camarillo, CA (US)

( * ) Notice: Subject to any disclaimer, the term of this patent is extended or adjusted under 35 U.S.C. 154(b) by 108 days.

(21) Appl. No.: 10/230,519

(22) Filed: Aug. 29, 2002

(65) Prior Publication Data

US 2004/0044267 A1 Mar. 4, 2004

(51) Int. Cl.$^7$ .............................................. A61M 31/00
(52) U.S. Cl. ........................................ 600/29; 604/60
(58) Field of Search .............................. 600/1, 7, 8, 29, 600/30; 604/158, 159, 164.07, 165.01–165.03, 171, 110, 264, 533–537, 544, 540, 523, 7, 8, 57, 59, 60–64; 606/108

(56) References Cited

U.S. PATENT DOCUMENTS

| | | | | |
|---|---|---|---|---|
| 4,326,520 A | * | 4/1982 | Alley | 604/171 |
| 5,599,291 A | * | 2/1997 | Balbierz et al. | 604/8 |
| 5,785,689 A | * | 7/1998 | de Toledo et al. | 604/165.01 |
| 5,893,837 A | * | 4/1999 | Eagles et al. | 604/9 |
| 6,228,059 B1 | * | 5/2001 | Astarita | 604/164.07 |
| 6,450,937 B1 | * | 9/2002 | Mercereau et al. | 600/7 |
| 6,450,938 B1 | * | 9/2002 | Miller | 600/7 |
| 6,554,760 B2 | * | 4/2003 | Lamoureux et al. | 600/7 |
| 6,569,077 B2 | * | 5/2003 | Schmidt | 600/7 |

* cited by examiner

Primary Examiner—Samuel G. Gilbert
(74) Attorney, Agent, or Firm—William L. Johnson

(57) ABSTRACT

A surgical instrument includes an elongated cannula having a forward expulsion end and a rearward breach end, arranged to include a bio-compatible material; a drive member arranged to urge the bio-compatible material in a reciprocating motion having two alternating phases; and a directional brake disposed to contact the bio-compatible material. The directional brake has a preferred braking direction for resisting motion of the bio-compatible material. The preferred braking direction of the directional brake is oriented to resist retreat of said material during the retreating phase and to allow advance of said material during the advancing phase, thus producing a net advance of the material to expel it from the expulsion end. The directional brake is disposed nearer to the expulsion end than the breach end of the instrument, to prevent undesired axial compression of the bio-compatible material during ejection.

8 Claims, 4 Drawing Sheets

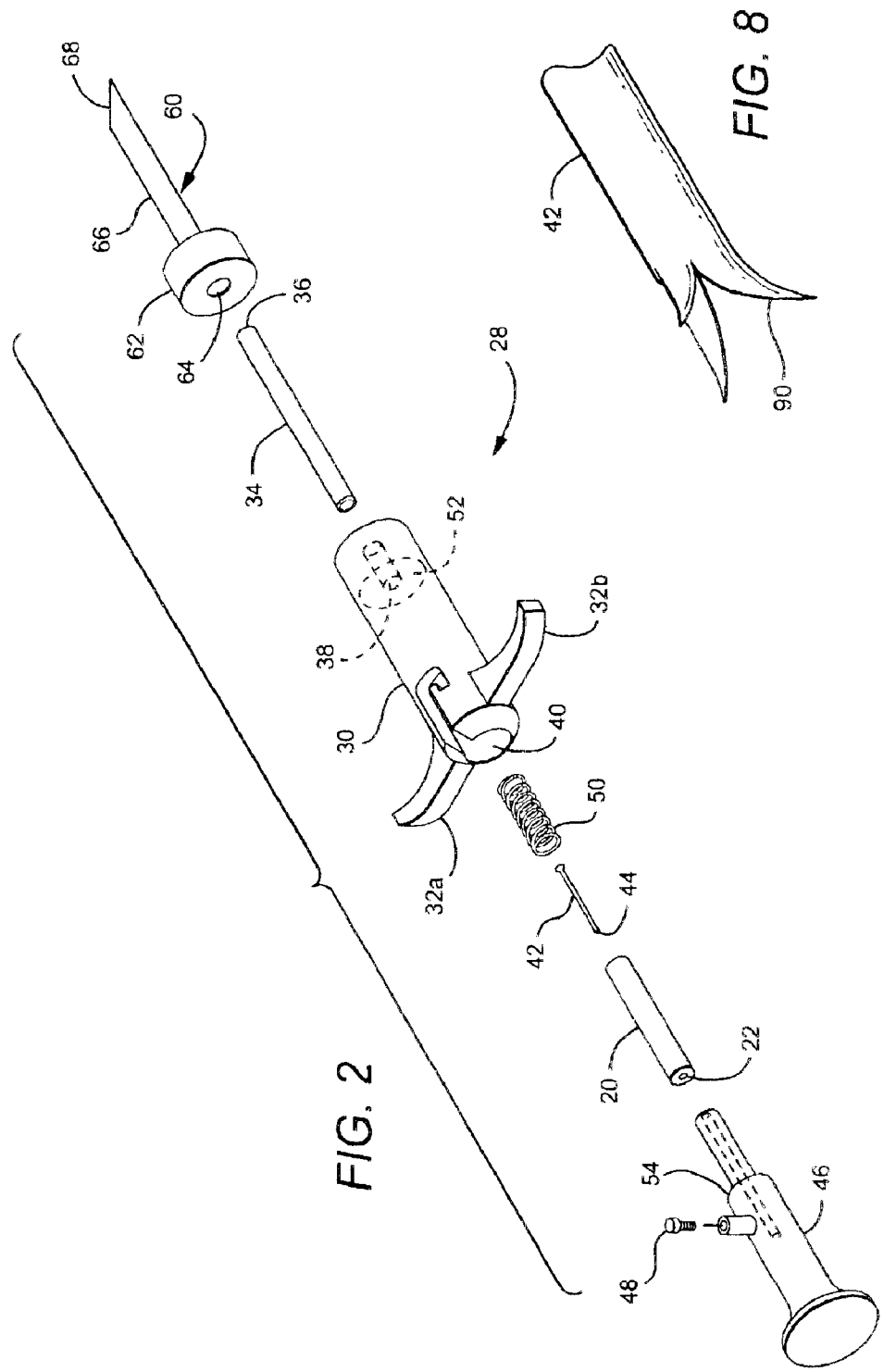

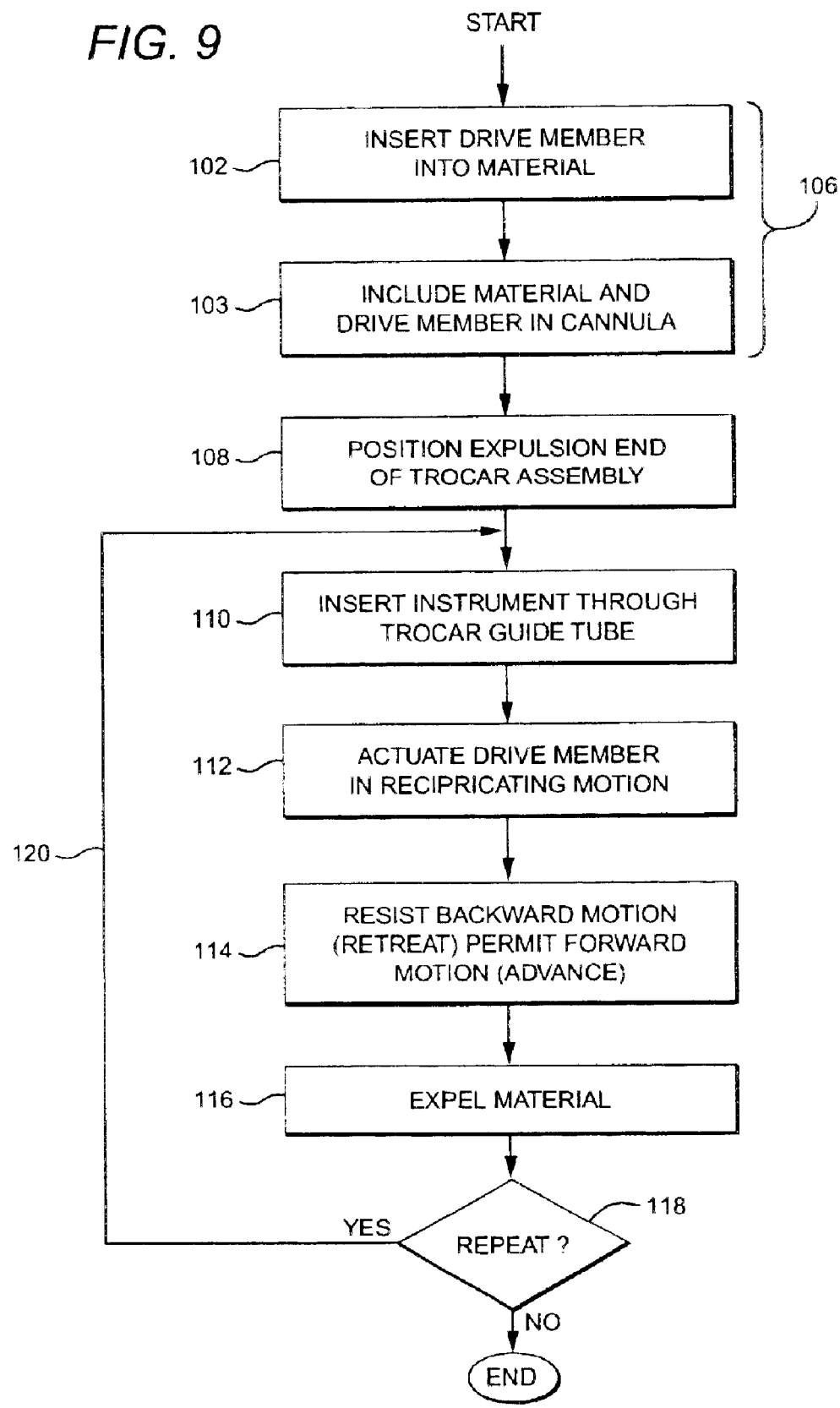

METHOD AND INSTRUMENT FOR SURGICAL DELIVERY OF BIOCOMPATIBLE MATERIALS

BACKGROUND OF THE INVENTION

1. Field of the Invention

This invention relates to surgical tissue augmentation in general and more specifically to methods and apparatus for surgical treatment of urinary incontinence by augmentation of the the bladder neck, the periurethral and sphincteric tissues near the bladder neck, the submucosal tissues of the urethra, or the tissues adjacent to the urethra.

2. Description of the Related Art

Millions of people suffer from urinary incontinence, which is the inability to voluntarily retain the urine in the bladder until release is appropriate. Although women are more likely to experience incontinence than men, the condition can affect either males or females of any age. A few of the common causes of incontinence are stroke, multiple sclerosis, prostate surgery, complications of chilbirth, and age. The problem often arises due to problems with the muscles that surround the urethra and retain the urine in the bladder. Many types of urinary incontinence are known, classified, and treated by a variety of methods, some surgical and some non-surgical.

Among the surgical procedures for incontinence are various types of implants: both implantable devices and materials for tissue augmentation. U.S. Pat. No. 5,562,598, for example, discloses an implantable device including a urethral cuff, a connecting tube, and an elastomeric bellows assembly. The device is closed by an external magnet placed on the skin over the implanted reservoir assembly. When the external magnet is in place the elastomeric bellows of the reservoir are compressed, and the prosthetic sphincter is closed. Removal of the external magnet from the skin over the implant allows the bellows to expand, thus opening the urethral cuff.

The magnetic device of U.S. Pat. No. 5,562,598 is obviously somewhat complex, and less convenient than normal voluntary control over the flow of urine. Indeed, any externally actuated device (and many are available) is inconvenient, undignified, and potentially embarrassing.

Many if not most patients would prefer a surgical method which would restore their normal ability to control urinary function through muscular contraction. Toward that end, procedures are available which employ tissue augmentation or "bulking" of the periurethral and sphincteric tissues near the bladder neck. For example, a collagen product sold under the trademark, "Contigen" is available. U.S. Pat. No. 6,277,392 to Klein (Aug. 21, 2001) describes a carbon-based biocompatible material for tissue augmentation of the tissues around the urethra. Small implantable devices such as that described in U.S. Pat. No. 6,231,501 to Ditter (May 15, 2001) are also known for enhancing a patient's ability to achieve voluntary muscular closure of the bladder outlet. Periurethral injection of Polytetrafluoroethylene (PTFE) has a known use in cosmetic enhancement surgery, see U.S. Pat. Nos. 5,607,477; 5,782,913; and 5,941,913 to Schindler et al. This material also shows promise as a method for bulking the tissues around the urethra.

One known method for urethral bulking employs an expanded polytetrafluoroethylene (PTFE) tubing. This tubing can be delivered into the periurethral tissue to augment the natural contraction of the urethral sphincters, thus aiding in bladder control. However, delivery of this material can be time consuming and difficult to control.

SUMMARY OF THE INVENTION

In view of the above problems, the present invention includes a method and apparatus for delivering implantable material in vivo, suitably for the treatment of urinary incontinence by bulking the periurethral tissues.

The apparatus of the invention includes an elongated cannula having a forward expulsion end and a rearward breach end, arranged to include the bio-compatible material; a drive member arranged to urge the bio-compatible material in a reciprocating motion having two alternating phases: a) an advancing phase during which said drive member urges said material toward said expulsion end, and b) a retreating phase in which said drive member substantially disengages said material and retreats away from said expulsion end; and a directional brake disposed to contact the bio-compatible material. The directional brake has a preferred braking direction for resisting motion of the bio-compatible material. The preferred braking direction of the directional brake is oriented to resist retreat of said material during the retreating phase and to allow advance of said material during the advancing phase, thus producing a net advance of the material to expel it from the expulsion end.

In a preferred embodiment of the invention, the directional brake is disposed nearer to the expulsion end than the breach end of the injector. It is most preferred that the directional brake be disposed substantially at the expulsion end of the injector. This prevents undesired axial compression of the implantable material during expulsion.

In one embodiment, the directional brake includes lanced features in the cannula with inwardly biased, sloped barb-like projections, or "teeth". These projections provide a sharp forward edge and a gently sloping rearward ramp much in the manner of a barb on a fishhook (or ratchets on a gear). The barb-like projections thus permit the implantable material to slide easily forward; on the other hand, they positively engage the material in response to any backward (toward the breach) motion of the material.

Other directional brakes could be substituted or included, such as imbricate, overlapped surface features, barb-like or toothed surface features, filamentary projections disposed with a preferred grain, or other directional braking mechanisms.

In some embodiments, the drive member comprises a thin rod or cable inserted axially inside the cavity of a tubular implantable material and is actuated in reciprocating forward and backward motion in relation to the cannula. The reciprocating motion is converted to a net forward motion by the directional brake, thus causing the material to advance and be ejected from the expulsion end of the injector.

The invention also includes a method of delivering an implantable material in vivo, comprising the steps of: including the material in an elongated cannula having a breach end and a forward expulsion end; positioning the forward expulsion end of the cannula at a desired site; urging the implantable material alternately forward and backward in a reciprocating motion cycle; directionally resisting the motion of said implantable material by producing a resistance to backward motion of said material while more readily permitting forward motion so that the material advances more than it retreats during each motion cycle. The directional resistance is most preferably disposed nearer to the expulsion end than the breach end of the injector.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 2 is an exploded perspective view of an apparatus in accordance with the invention, showing external form and features in relation to a surgical trocar assembly positioned to accept insertion of the apparatus;

FIG. 8 is a perspective view of a suitable drive member with three-fold, directionally engaging features; and FIG. 9 is a flow diagram of a method in accordance with the invention.

DETAILED DESCRIPTION OF THE INVENTION

The invention includes a method and apparatus for delivering Bio-compatible, implantable material in vivo, suitable for the treatment of urinary incontinence by bulking the periurethral tissues and sphincteric tissues near the bladder neck, thus allowing full secure closure of the bladder. However, the apparatus and methods described are not necessarily limited to urological treatments. The invention is suitable for delivering a variety of implants, particularly tubular implants, which might be desired in any surgical context. Applications may exist in vascular, cosmetic or internal reconstructive surgery, for example.

The following definitions are offered as aids to understanding the terminology of the disclosure, but are in no way intended to limit the scope of the words included therein. To the extent the definitions offered herein expand the ordinary understanding of the terms, the expanded definition is intended. In any other case the offered definition is intended to augment and not to limit the ordinary definitions and any definitions customary in the related arts.

Brake: any mechanism or feature, active or passive, which tends to resist motion in at least some direction of some object, component, member or material;

Directional Brake: a brake as defined above which tends to resist motion preferentially, so that motions in a certain preferred direction (or directions) are resisted more than motions in other directions;

Cannula: an elongated tube, duct or needle having a substantially axial or longitudinal channel, capable of including the implant material. The cannula may suitably be (but need not necessarily be) substantially cylindrical.

Drive member: a device, mechanism or member which transmits force or tends to impart motion to another member or material, including but without limitation a shaft, tube, rod, wire or cable;

Lancing: any method of fabricating an internal tab or projection (for example, in a tube or cannula by striking the external surface with a sharp object to pierce the surface, thereby cutting an outline of the projection). Also can be used to refer to the product of any such fabrication technique.

Figure 1:
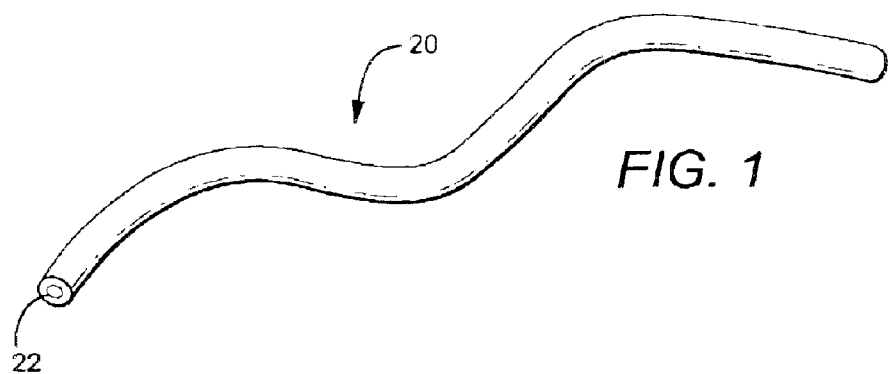
FIG. 1 is a perspective view of a typical form of biocompatible, implantable material suitable for use with the invention.

The invention is particularly suited to the delivery of an implantable material substantially as shown in FIG. 1. This implantable material is typically supplied in the form of an elongated tube 20, with an internal channel 22. The dimensions could vary along the length of the tube. Flexible and somewhat compressible materials are most suited to the invention. It is not necessary that the tube be cylindrical as shown: arbitrary cross sections could be used, but for simplicity we illustrate the case for a substantially cylindrical, elongated, flexible tubular implant.

A typical segment or length of the implantable material is 50 to 200 mm long (for a urinary bulking procedure). For such procedures an inside diameter of about 1 millimeter is suitable, with an outside diameter in the neighborhood of 2.4 millimeters. Slits, openings and variations in the surface can be provided optionally, to encourage tissue ingrowth.

A typical bio-compatible implant material suitable for use with the invention is a tubular form of expanded polytetrafluoroethylene (PTFE). This material is flexible, and can accept an unusually large degree of longitudinal compression while responding with a small degree of radial expansion. However, the invention is not limited to use with this material: other biocompatible materials could be used with only slight adaptation of the apparatus and method.

The plastic qualities of a flexible implantable material, particularly of tubular expanded PTFE, prove a challenge to the method and apparatus which must reliably and quickly deliver the material. The difficulty arises from the compressibility of the material. It becomes difficult to push a sufficient length of such a material from behind: by analogy, it is proverbially difficult to "push a rope." Even confinement in a cylindrical housing or cannula does not completely solve the problem. When pushing an elongated volume of deformable material, the material tends to compress, forming compressed, dense plugs rather than advancing forward in a uniformly expanded, low density tube. This is very undesirable, particularly because the resulting high density plugs are relatively hard and tough, occupy little volume, and do not re-expand after implantation. These hard plugs are poorly suited to bulking applications because they lack both volume and resilience. It is greatly preferable to deliver the implant material as an expanded, high volume tube.

An apparatus suitable for delivering the implant material in accordance with the invention is shown generally at 28 in FIG. 2. A grippable housing 30 preferably has wing like features 32a and 32b for an operator's fingers. An elongated narrow cannula 34 projects forward from the housing 30, terminating in an expulsion end 36 from which implantable material can be expelled. At the opposite or rearward end 38 the housing 30 has a breach opening 40 to receive the implantable material 20.

An elongated drive member 42, for example a thin metal rod or tube, is sized to thread through a central axial canal or lumen in the implantable material 20, which in turn slidably surrounds the drive member like a coaxial sleeve. In a manually actuated embodiment as shown, the rearward end 44 of the drive member 42 preferably fits into a cavity in a plunger 46 and is secured thereto, for example by a setscrew 48. A helical coil spring 50 can also be provided to aid in actuating the drive member in a reciprocating motion, as described in detail below. When the instrument is assembled, the spring is compressed between a first shoulder 52 (at the breach opening of the grippable housing 30) and a second shoulder 54 on the plunger 46.

One method of positioning the instrument employs a surgical trocar assembly, shown generally at 60. Such surgical trocars are in widespread use and are commercially available from a number of sources. A typical assembly includes a lock 62 having a breach orifice 64, and a hollow trocar guide tube 66 typically terminating at a bias-cut forward end 68. The instrument of the invention 28 can suitably be sized so that the cannula 34 is insertable via the breach orifice 64 of the trocar assembly 60.

In one suitable method of surgically positioning the instrument 28 a sharpened, rodlike trocar implement (not shown) is inserted through the breach opening 64 of the trocar lock 62 and pushed through the guide tube 66 until a sharpened point projects forward from the forward end 68 of the guide tube 66. The trocar assembly can then be thrust firmly forward, penetrating tissue with the aid of the sharpened point of the trocar until the desired surgical location is attained. In more difficult applications surgical incisions may also be required to properly insert the trocar assembly.

In a typical operation, additional instruments may be required in connection with the instrument 28: for example, an optical viewing means may be attached in fixed relation to the instrument 28; alternatively, the instrument 28 may be held in fixed relationship to a cystoscopic instrument. Other means of guidance could be used, such as radiological or ultrasonographic imaging techniques. Optionally, in some applications after initial penetration into the tissue, the sharp trocar may be withdrawn and viewing instruments such as an optical or fiber optic viewing scope could be inserted via the breach end 64 through the guide tube 66. The proper insertion and positioning of the instrument is not the focus of this invention, but can be accomplished by well known surgical methods appropriate to a specific procedure. Some methods are mentioned here only to explain the motivations for inserting various known instruments through the breach opening and guide tube of the trocar assembly.

After the forward end 68 of the guide tube 66 is positioned, the sharp trocar implement or other guiding instrument is withdrawn from the trocar lock 62 and guide tube 66. When it is desired to deliver the implantable material 20, an instrument 28 in accordance with the invention is inserted through the orifice 64.

Figure 3:
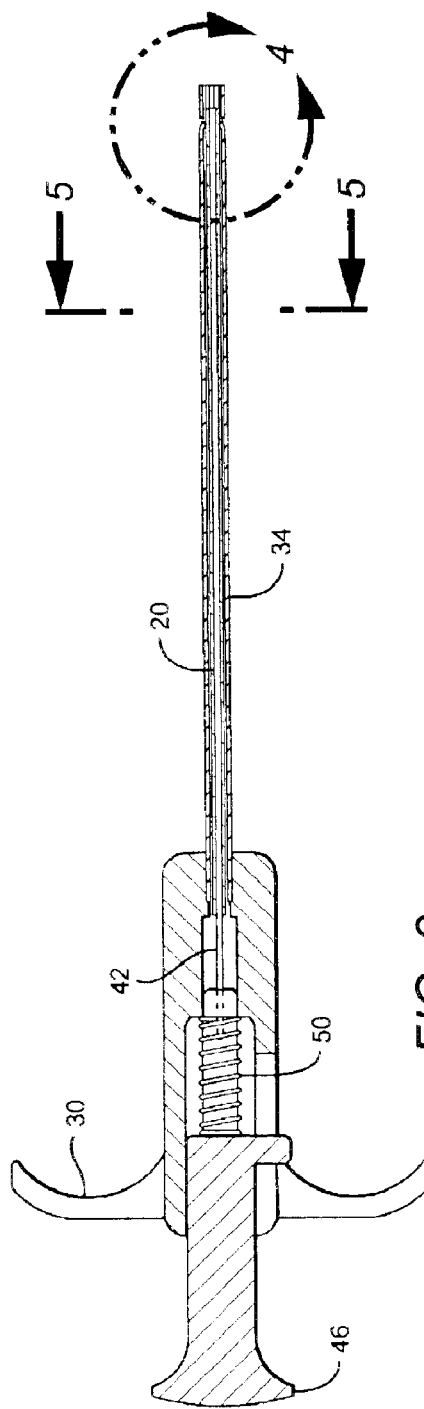
FIG. 3 is a sectional view of an apparatus in accordance with the invention, with internal parts assembled.

The assembled instrument 28 is shown in FIG. 3 in longitudinal sectional view. the tubular cannula 34 is fixed to the grippable housing 30. The cannula should suitably be sized for a running or sliding fit between the cannula and the trocar guide tube (shown in FIG. 2). (For definition of "running or sliding fit," see Oberg, E., *The Machinery's Handbook*, $22^{nd}$ Edition, (Industrial Press Inc., New York), p. 1527) The cannula 34 in turn surrounds and includes a length of the implantable material 20. A thin, axial rod or shaft (the "drive member" 42) is inserted through the central axial channel 22 in the implantable material 20. The drive member 42 could suitably comprise a rod, shaft or very small tube, but it could also be solid or stranded wire or cable. A metal such as stainless steel is suitable for the drive member 42, but other durable and sterilizable materials could be used. More details of the essentially coaxial assembly of cannula, material, and rod are discussed below in connection with FIGS. 4 and 5.

At the breach end of the instrument, the plunger 46 is fixed to the drive member 42 in such a way that forward or rearward longitudinal movement manually imparted to the plunger 46 is transmitted to the drive member 42. The spring 50 is arranged in front of the plunger 46 and confined between it and a forward annular shoulder 38 formed within the breach cavity of the housing 30. Thus, forward motion of the plunger 46 tends to compress the spring 50; when the spring 50 is released, elastic return causes the plunger 46 and drive member 42 to return to their original position. This plunger and return action allows a surgeon to manually pump the plunger in a reciprocating or alternating manner, thereby imparting a reciprocating motion to the drive member 42.

Obviously, innumerable variations on the plunger and spring mechanism are possible which equivalently facilitate imparting a reciprocating or alternating motion to the drive member 42. Such variations are within the scope of the invention. Further, other more sophisticated mechanisms could be used to impart an reciprocating motion to the drive member: for example, and not by way of limitation, electromechanical vibrators, stepper motors, rotating cams, piezoelectric linear motors, and the like. All such mechanisms are encompassed within the scope of the invention.

Figure 7:
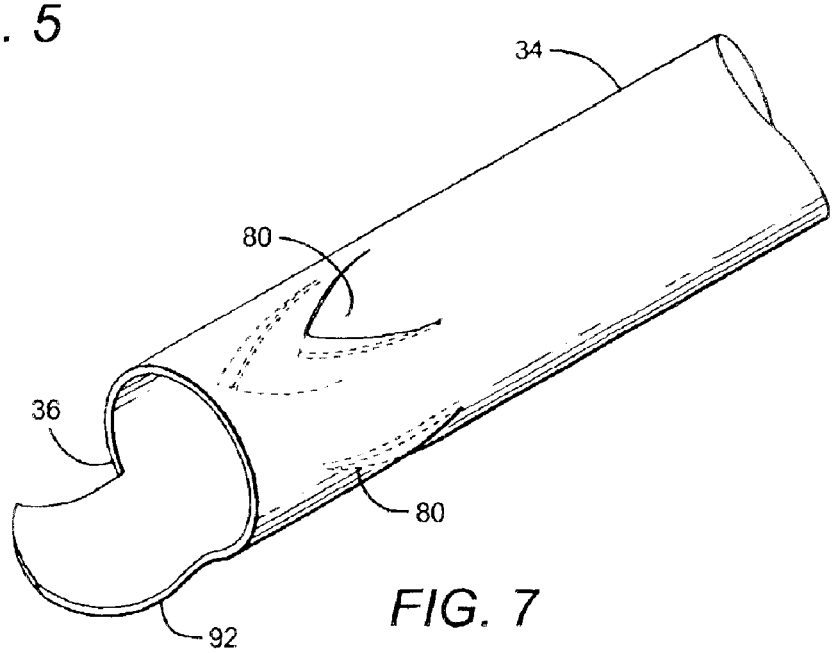
FIG. 7 is a greatly magnified perspective view of the cannula in the apparatus of FIG. 2, showing a suitable directional brake fabricated by lancing tooth-like, inward facing projections into the cannula.
Figure 4:
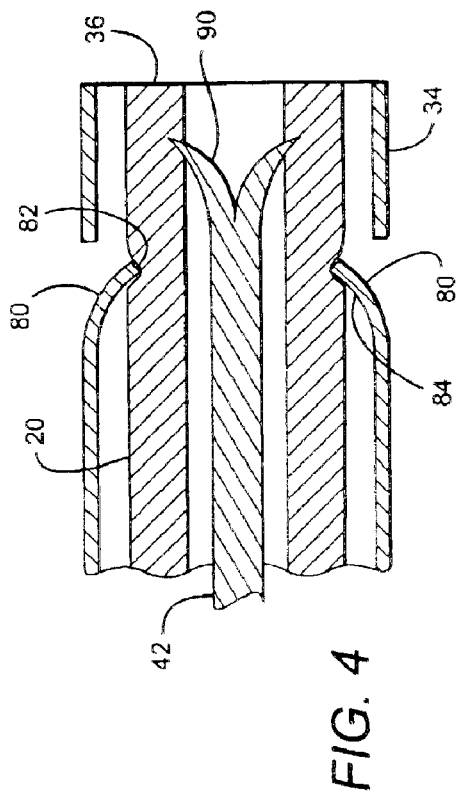
FIG. 4 is an expanded detail of the sectional view of FIG. 3, more clearly showing a directional brake, material, and an drive member.
Figure 6:
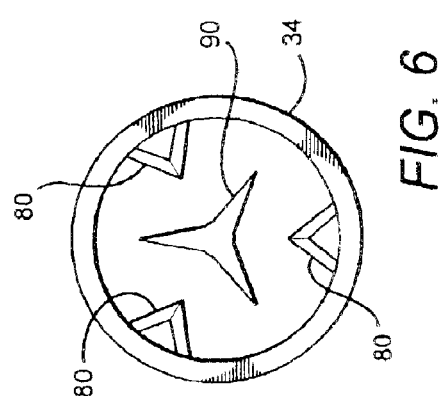
FIG. 6 is an end view, looking axially down the cannula from the expulsion end of the cannula, showing a suitable three-fold arrangement of inward projections (of the cannula), staggered in relation to three directional engaging features (of the drive member)

FIG. 4 shows more clearly the details of a directional brake which converts the reciprocating or alternating motion of the drive member 42 into linear forward motion to expel the implantable material 20 from the expulsion end 36 of the cannula 34. As that figure shows, the cannula 34 is in a typical embodiment provided with lanced (inwardly bent) projections 80. These projections 80 are disposed with a sharp forward edge 82 and a gently sloping rearward ramp 84, much in the manner of a barb on a fishhook (or ratchets on a gear). Although FIG. 4 shows two projections, diametrically opposed, the actual number of projections intersected by any section line will depend on the placement and spacing of the projections in a particular embodiment. A different arrangement is illustrated in FIGS. 6 and 7, discussed below. The barb-like projections 80 encourage the implantable material 20 to advance; on the other hand, they sharply engage the material in response to any backward (toward the breach) motion of the material, thereby impeding retreat of the material 20.

Described more generally, the cannula 34 is in accordance with the invention equipped with a directional brake (such as projections 80) which resists backward slippage of the material but tends to permit forward motion of the material. The brake could be provided by various methods besides the lanced barbs 80 shown in the figures. For example, directional surface textures could be provided on the inward facing surface of the cannula 34. Fishscales, imbrication, barbs, skewed ridges, sawtooth patterns and other textures are known which tend to resist motion across a surface in a preferred direction. Hairlike filamentary projections with a preferred "grain" (like sealskin) could also be used. Overlapped designs such as the familiar shingle roof could be employed. All such variations are contemplated within the scope of the invention.

The dynamic operation of the instrument 28 is as follows: the operator imparts a reciprocating or alternating axial forward/backward motion via the plunger 46 and spring 50 to the drive member 42. This drive member 42 is fitted tightly inside the tubular implantable material 20 and thus tends to urge the material alternately forward and backward in a reciprocating motion. The material is surrounded by the cannula 34 which is held fixed in relation to the guide tube 66 and movable in relation to the drive member. In response to the reciprocating urging of the material, the barb-like projections 80 in the surrounding cannula 34 provide a directional brake which strongly resists backward slippage of the material on the rearward half of the cycle, while permitting forward slippage during the forward half of the cycle. Thus the net response of the material 20 is to advance, which causes it to be expelled from the expulsion end 36 of the cannula 34 (and the forward end 68 of the guide tube 66).

It is extremely preferred that the directional motion-resisting brake be disposed nearer to the expulsion end 36 than the breach end 38 of the instrument. This has been found greatly more effective in effecting forward expulsion of the material without producing linear axial compression of the implantable material. It is most preferred that the motion-resisting brake be disposed substantially at the expulsion end of the cannula 34 (and guide tube 66); in practice it is sufficient in many applications to dispose the brake within about 2 centimeters from the expulsion end. This position allows the apparatus to pull the tubular implantable material through the cannula 34, rather than trying (as in prior devices) to push the material using pressure from behind (in the manner of a hypodermic injector). Pushing the material through the tube results in the material being axially compressed, so that it is expelled in a dense form, poorly adapted for bulking applications. This problem is particularly acute with expanded PTFE or other spongy, compressible and resilient material. Thus, the method of the invention is particularly suited to expanded PTFE and other soft or spongy materials.

It is also extremely preferable that the resisting brake and indeed, the entire mechanism of expulsion, operate without significant rotation about the axis of the cannula. Any screw-like or torqueing mechanism tends to impart torque to the tubular implant material. The resulting twist of the tubular implant material interferes with its expulsion. It is important to deliver the material in an expanded form for it to be surgically most beneficial. Accordingly, in a preferred embodiment of the invention the apparatus operates by linear axial motions primarily, and without significant rotation about the long axis of the implantable tubular material 20.

In one embodiment, as FIG. 4 also shows, the drive member 42 has a directional engaging feature 90 such as outwardly flaring barbs or prongs substantially near the expulsion end of the apparatus. This engaging feature 90 tends to aid the drive member in obtaining purchase inside the tubular implant material to push the material forward. Alternatively, barbs, overlapped conical shoulders (in a sawtooth pattern) or directional texture could be provided on the rod which would tend to resist motion of the tubular implant material backward with respect to the rod. Generally stated, the drive member optionally includes a directional engaging feature or texture which improves purchase or engagement between the material and the drive member for forward urging of the material by the drive member. Such directional engaging features should most preferably be disposed substantially near the expulsion end of the apparatus, for the same reasons discussed above in connection with the directional brake and the cannula.

It will be apparent that several variations of the apparatus could be equivalently used. For example, the apparatus could be modified so that the cannula is moved alternately forward and backward, while the rod remains fixed. In another variation, the cannula and rod could both be moved in alternating fashion backward and forward (relative to one another). These and other variations are equivalent to and within the scope of the invention. A small tube could in some embodiments be substituted for the inner rod without departing from the invention.

It should also be noted that in some embodiments one or more of the components could comprise flexible elongated elements. The elongated elements including drive member 42 and cannula 34, are not necessarily required to be rigid in all embodiments, nor are they required to be substantially linear. Bent, curved and even recurved variations of the elements could be used (with flexible inner elements in some embodiments) and are contemplated to allow a surgeon to reach difficult anatomical locations and orientations.

Figure 5:
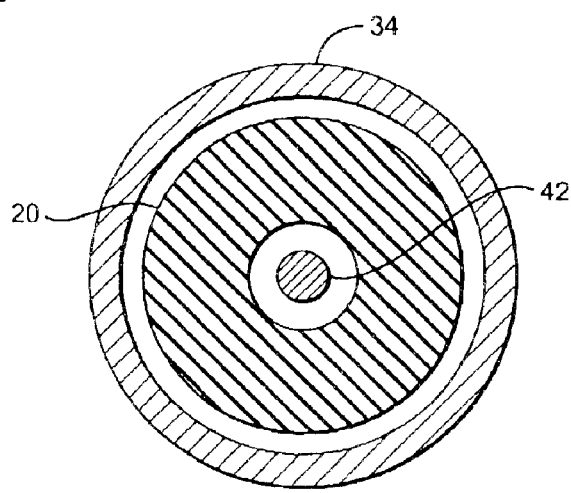
FIG. 5 is an (enlarged) axial cross section taken across section line 5 of the apparatus in FIG. 3.

FIG. 5 shows a cross section of the assembly of the cannula 34, material 20 and drive member 42. These components are suitably assembled as shown in substantially cylindrical, coaxial layers. The lanced projections, 80 which comprise an embodiment of a directional motion resisting brake, are more easily seen in FIGS. 6 and 7. In a typical embodiment, the cannula 34 comprises a stainless steel material and the lanced projections are formed by cutting the shape of the lance with EDM (Electrical Discharge Machining) then pushing the projections into the cannula to create an internal tab. Other methods could be used, such as drawing a tube with lanced projections in place.

FIG. 6 shows an end view, looking along the axis of the cannula from the expulsion end, of a particular embodiment of the invention. The material 20 is omitted so as not to obstruct the view of the barb-like projections 80 (comprising the directional brake) and the engaging feature 90 (of the drive member 42). In this particular embodiment the projections 80 are at least three, spaced substantially 120 degrees apart from one another in a three-fold, symmetric pattern. More than one rank of such projections could be provided, with corresponding projections lining up in file (in rows). The engaging feature 90 is in this embodiment also three-fold, suitably comprising three outwardly flaring or flexed barbs arranged 120 degrees apart from one another around the longitudinal axis of the drive member. As FIG. 6 shows, it is advantageous to dispose the barbs of the engaging feature so that they are staggered relative to the Projections 80 of the directional brake. In this arrangement the barbs of the engaging feature can be pushed forward by the drive member without interference from the inwardly flexing projections 80. Thus, when the drive member moves forward, the engaging feature 90 it engages the material 20 and carries it forward. When the engaging feature reaches the point of the inwardly flexing projections 80 (of the cannula) the three-fold barbs pass between the projections 80 without interference. Similarly, the drive member can easily retreat without interference, thanks to the staggered arrangement of the projections 80 relative to the barbs of the engaging feature 90.

It will be apparent that other arrangements can be devised which also offer the advantages of staggering the lobes of the engaging feature with the projections 80. Two-fold, four-fold, irregular, and even more complex geometries could be devised without departing from the scope of the invention.

The three-fold symmetrical cannula of FIG. 6 is shown in perspective in FIG. 7. FIG. 7 also shows an optional feature which is included in some embodiments of the invention: A curved projection 92 may be disposed substantially at the ejection end of the instrument. In connection with the cannula 34, and preferably integrally formed with the cannula, the projection 92 extends forward in an arc or at an angle with respect to the long axis of the cannula. As the material is expelled from the instrument, the protruding projection 92 tends to cause the material to adopt a controlled or predetermined curl (for example, to encourage a non-linear implantation or some other pre-determined bulking pattern). FIG. 8 shows a forward end of the drive member 42 also depicted in FIG. 6 and suitable for use in connection with the cannula of FIG. 7. Outwardly flaring, three-fold engaging features 90 are apparent at the forward end of the drive member 42.

According to one aspect of the invention, all or part of the apparatus described above (at least the cannula and material) could be pre-assembled and loaded with a predetermined load of bio-compatible material. Preferably the entire instrument 28 could be pre-loaded, assembled, sterilized and packaged as a surgical module for convenient use. Such modules could be provided either as disposable or as recyclable products, either with a trocar assembly or for use with available trocar assemblies.

An embodiment of a method in accordance with the method aspect of the invention is shown in FIG. 9.

Preliminary steps 102 and 103 are not essential steps in every claimed embodiment of the method. Nevertheless, in order to completely describe the method of using the invention, the pre-surgical assembly steps 102–103 are shown in FIG. 9 and described herein. Although an apparatus (as described above in connection with FIG. 2) could be loaded during a surgery, to do so would be inefficient and unduly time consuming. Rather, a pre-assembled and loaded apparatus should preferably be prepared (either by a manufacturer or other personnel) in advance of the surgery. Thus, the pre-surgery assembly steps 102 through 103 should preferably be performed in advance of the surgical procedure.

Preliminarily, a length of implantable material is loaded (steps 102, 103) into an injecting apparatus of the invention. In some embodiments, some or all of the cannula, the drive member, the material, and optionally any or all other elements of the instrument 28 are provided in a pre-loaded, assembled, sterilized and packaged module for ease of use during surgery. One suitable loading sequence is as follows: preferably the drive member 42 is first inserted through the axial channel of the implantable material 20 (step 102) from the forward (expulsion) end; the material and drive member are next included in the cannula by inserting the material and drive member into the cannula 34 from the rearward or breach end (step 103), preferably while respecting the direction of the directional brake (lancings, for example). Steps 102–103 collectively comprise a step of loading the implantable material (106). Optionally, the loaded instrument 28 is then sterilized and packaged to maintain sterility.

The implantable tubular material 20 is suitably made of expanded PTFE (as previously described), and can optionally be axially compressed during insertion into the cannula 34. It has been found that, for example, 20 linear cm of material can suitably be compressed into 10 linear cm in a cylindrical cannula. Later (in step 116) the material is expanded upon expulsion from the expulsion end of the guide tube, regaining its original dimension without significant distortion.

The following steps are performed during the surgical procedure to implant the material in a patient. First a trocar assembly is inserted into the patient (step 108) with the forward end positioned at a site where the implantation is desired, in accordance with the surgical and medical arts applicable to implantation of bulking materials. This step may include use of a sharp trocar implement to penetrate tissue, or other surgical techniques could be employed. Various means of guidance could optionally be employed. Next, any trocar implement is withdrawn from the breach end of the trocar assembly 60. If the instrument 28 of the invention has not previously been loaded as a pre-packaged module, it must at this point be loaded for use. The cannula 34, material 20, and drive member 42 are inserted (step 110) via the breach end (64 in FIG. 2) of the trocar assembly 60 and slid forward through the trocar guide tube 66 until the expulsion end 36 of the cannula 34 is positioned near the expulsion end 68 of the guide tube. Optionally, a locking collet or similar stop can be provided at a measured position on the cannula, to secure the cannula against unintentional insertion beyond the proper depth. This step also positions the motion resisting brake near the expulsion end. The instrument is now in position for use.

Next, in step 112, the operator activates a mechanism to actuate the drive member alternately forward and backward in a reciprocating axial motion. In a manual embodiment (shown in FIG. 2 above) this activation would typically comprise moving the plunger in alternating pumping motion. Depending on the embodiment, this motion is mechanically imparted to at least one of the drive member and/or the cannula.

In response to the motion of the drive member, the material is urged alternately forward and backward. In step 114 a motion resisting brake preferentially resists the rearward motion of the bio-compatible material by a directional resistance, this resistance having a preferred direction which more readily permits forward motion than rearward motion of the material. Because of the directional resistance, the implantable material tends to advance in a net forward motion in response to the reciprocating motion cycle causing the material to be expelled from the expulsion end of the cannula. Thus, the directional resistance (brake) converts a reciprocating motion into a net forward linear motion of the material, thereby expelling (step 116) the implant material from the expulsion end of the apparatus.

After expelling the implant material, the surgeon can make a decision (118) to reload if desired and further augment the implant (returning by return path 120); or he can terminate the operation and remove the instrument. Various imaging modalities could optionally be employed to determine when the proper amount of implant has been delivered and to verify the position of the material.

While several illustrative embodiments of the invention have been shown and described, numerous variations and alternate embodiments will occur to those skilled in the art. For example, the cannula 34 could be integrated with the guide tube 66, or the inner surface of the guide tube could have features which perform the functions of the cannula (including the motion resisting brake). The method of actuating the instrument in reciprocating motion could easily be varied, and could be automated in numerous ways: for example, and not by way of limitation, electromechanical vibrators, reciprocating motors, stepper motors or transducers could be arranged to actuate the drive member or cannula in reciprocating motion. The cannula, drive member, or guide tube could be flexible to varying degrees, or the instrument could be hooked or curved to reach difficult anatomical positions. Various cutting, measuring or other surgical tools could be integrated with, combined with or used in combination with the apparatus and method described. Such variations and alternate embodiments are contemplated, and can be made without departing from the spirit and scope of the invention as defined in the appended claims.

We claim:

1. A method of delivering a bio-compatible material in vivo, comprising the steps of:

including said material in an elongated cannula having a forward expulsion end and a rearward breach end;

positioning the forward expulsion end of said cannula at a desired site;

urging said bio-compatible material alternately forward and rearward in a reciprocating motion cycle; and preferentially resisting the rearward motion of said bio-compatible material by a directional resistance, said resistance having a preferred direction which more readily permits forward motion than rearward motion of the material so that said material tends to advance in a net forward motion in response to said motion cycle causing the material to be expelled from said expulsion end;

wherein said directional resistance is disposed nearer to said expulsion end than said breach end of said cannula.

2. The method of claim 1, wherein said directional resistance is located substantially at the expulsion end of the cannula.

3. The method of claim 1, wherein said material comprises a tubular implant material, and said urging of said material is performed by moving in a reciprocating cycle an axial elongated member inserted through said tubular implant material.

4. The method of claim 3 wherein said material comprises tubular expanded polytetrafluoroethylene.

5. The method of claim 3, wherein said directional resistance is provided by said cannula surrounding said bio-compatible material, said cannula having at least one barb-like lancing which tends to sharply engage said material in response to any retreat, while sliding more freely in response to advance of said material.

6. The method of claim 3, wherein said directional resistance is provided by a cannula having a directional surface texture inwardly disposed toward said material.

7. The method of claim 3, wherein said urging of said material is actuated by manually moving a plunger in an reciprocating manner.

8. A ready to use, pre-prepared and loaded surgical implant module, suitable for insertion via a breach loadable surgical trocar assembly, comprising:

an elongated length of tubular implant material, included in a substantially cylindrical cannula;

said cannula having inwardly protruding features which tend to resist retreat of said material, while substantially permitting advance of said material; and an elongated drive member inserted through an axial channel in said tubular implant material and communicating with a mechanism for actuating said elongated drive member in a reciprocating axial motion.

* * * * *